(12) United States Patent
Aguerre et al.

(10) Patent No.: US 9,795,535 B2
(45) Date of Patent: Oct. 24, 2017

(54) ROBOTIZED SYRINGE ACTUATOR

(71) Applicant: KIRO ROBOTICS, S.L., Arrasate (Gipuzkoa) (ES)

(72) Inventors: Jean-Philippe Aguerre, Itxassou (FR); Gorka Garcia Echevarria, Elorrio (Bizkaia) (ES); Alaitz Cristobal Izagirre, Aretxabaleta (Gipuzkoa) (ES); Susana Soto Iglesias, Arrasate-Mondragon (Gipuzkoa) (ES); Borja Lizari Illarramendi, Araico (Burgos) (ES); Naiara Telleria Garay, Arrasate-Mondragon (Gipuzkoa) (ES)

(73) Assignee: KIRO GRIFOLS, S.L., Arrasate (Gipuzkoa) (ES)

( * ) Notice: Subject to any disclaimer, the term of this patent is extended or adjusted under 35 U.S.C. 154(b) by 0 days.

(21) Appl. No.: 14/718,870

(22) Filed: May 21, 2015

(65) Prior Publication Data
US 2015/0335530 A1    Nov. 26, 2015

(51) Int. Cl.
| | | |
|---|---|---|
| *A61J 1/16* | (2006.01) | |
| *A61J 1/20* | (2006.01) | |
| *B65B 3/00* | (2006.01) | |
| *A61M 5/145* | (2006.01) | |

(52) U.S. Cl.
CPC .............. *A61J 1/16* (2013.01); *A61J 1/2096* (2013.01); *A61M 5/1452* (2013.01); *B65B 3/003* (2013.01); *A61M 5/1456* (2013.01); *A61M 5/14566* (2013.01); *A61M 2005/14573* (2013.01); *A61M 2209/045* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,022,207 A | | 5/1977 | Citrin | |
| 4,155,490 A | * | 5/1979 | Glenn | ........................ B01L 9/54 128/DIG. 1 |
| 5,219,099 A | * | 6/1993 | Spence | ............... A61M 5/1456 222/325 |

(Continued)

FOREIGN PATENT DOCUMENTS

| | | |
|---|---|---|
| EP | 1825875 A1 | 12/2012 |
| ES | 1003629 U | 7/1988 |

(Continued)

OTHER PUBLICATIONS

Search Report for Spanish Application No. 201430746 dated Nov. 12, 2015.

(Continued)

*Primary Examiner* — Larry E Waggle, Jr.
*Assistant Examiner* — Alvin Grant
(74) *Attorney, Agent, or Firm* — Knobbe Martens Olson & Bear LLP

(57) ABSTRACT

A robotized syringe actuator has a holding clamp for holding the peripheral flange of the opening of the tube or the flange at the end of the syringe plunger, by applying simultaneous pressure to both faces of the tube flange or of the syringe plunger flange. The actuator has a holder for the syringe cylinder which has a housing for receiving the syringe tube.

14 Claims, 16 Drawing Sheets

(56) References Cited

U.S. PATENT DOCUMENTS

| | | | | |
|---|---|---|---|---|
| 5,647,851 A * | 7/1997 | Pokras | A61M 5/20 | 604/131 |
| 5,944,709 A * | 8/1999 | Barney | A61J 1/10 | 206/219 |
| 6,063,194 A * | 5/2000 | Poliniak | A61J 3/00 | 118/623 |
| 6,076,333 A * | 6/2000 | Stoker | B65B 55/027 | 53/425 |
| 6,287,595 B1 * | 9/2001 | Loewy | A61J 3/00 | 424/451 |
| 6,303,143 B1 * | 10/2001 | Chrai | A61J 3/00 | 424/451 |
| 6,387,077 B1 * | 5/2002 | Klibanov | A61M 5/1456 | 128/DIG. 1 |
| 7,338,472 B2 * | 3/2008 | Shearn | A61M 5/1456 | 604/155 |
| 8,206,335 B2 * | 6/2012 | Pruitt | A61M 5/31586 | 222/309 |
| 2002/0081748 A1 * | 6/2002 | Roberts | A61M 15/00 | 436/174 |
| 2004/0103951 A1 * | 6/2004 | Osborne | B65B 7/2821 | 141/27 |
| 2010/0107570 A1 * | 5/2010 | Khan | B65B 9/18 | 53/479 |
| 2010/0298768 A1 * | 11/2010 | Halili, Jr. | A61J 1/2096 | 604/87 |
| 2010/0326020 A1 * | 12/2010 | Schmaelzle | A61J 1/1437 | 53/471 |
| 2011/0186177 A1 * | 8/2011 | Lanier, Jr. | A61J 1/2065 | 141/383 |
| 2012/0241043 A1 * | 9/2012 | Perazzo | A61J 7/0053 | 141/2 |
| 2013/0085467 A1 * | 4/2013 | Capelli | A61J 1/14 | 604/416 |

FOREIGN PATENT DOCUMENTS

| | | | |
|---|---|---|---|
| GB | 2356349 A | 5/2001 | |
| JP | EP 1825875 A1 * | 8/2007 | A61M 5/14546 |
| WO | WO 2004/011056 A2 | 2/2004 | |

OTHER PUBLICATIONS

Search Report for European Application No. EP15382258 dated Jan. 1, 2016.

* cited by examiner

ROBOTIZED SYRINGE ACTUATOR

CROSS-REFERENCE TO RELATED APPLICATION

This application claims priority to Spanish Patent Application No. 201430746 filed on May 21, 2014, the disclosure of which including the specification, the drawings, and the claims is hereby incorporated by reference in its entirety.

The present invention relates to a robotized syringe actuator.

Syringes are usually formed by a tube inside which a plunger passes which is used to impel the liquid or gas contents inside the tube to one of the ends thereof which has an orifice connected to a needle or similar (a Luer-Lock, closed transfer device, etc.). The syringe can also be used to draw substances into the tube via the device connected to the outlet orifice. The opening through which the plunger is introduced into the tube usually has a peripheral flange. The outer end of the plunger also usually has a peripheral flange.

Syringe actuators are robotized units which usually form part of machines for handling, mixing, reconstituting and/or preparing medicinal substances, pharmaceutical products and/or medications. Syringes are used in these machines as elements for extracting the substance from the container that contains it and infusing said substance (or a mixture thereof) into other intermediate and/or final containers. On occasion, the syringe itself may be the initial and/or final container.

Spanish patent ES2138089 discloses a robotized system of such type for mixing said substances. In particular, this document discloses a system for mixing with a solvent a powder contained in a vial. The solvent is inserted into the vial by means of a syringe. The robotized mechanism for holding the syringe positions the syringe vertically with the needle in the lower position. The tube of the syringe is held by a pair of arms, and has an actuator of the piston of the syringe which acts on the piston flange. The actuator moves a housing into which the flange of the plunger enters along a groove. The flange of the tube of the syringe is also in a housing which is accessed along a groove.

PCT patent WO2013/0219386 discloses a device for mixing infusions which carries out at least a portion of the mixing automatically. The syringe is handled by a robotic arm which has a moving stop which only allows the plunger to be pushed down to its lower position.

PCT patent WO1994/04415 discloses an apparatus for dispensing biologically hazardous substances. The actuator has a pair of fixed flanges which allow the plunger flange to be actuated by applying pressure to a face of the flange or to the opposite face. Therefore said flanges do not hold the syringe.

Finally, all the known actuators from the prior art hold the syringe exclusively by some fixed portion or portions of the tube and actuate the plunger upwards or downwards by alternately pushing one or other face of the flange of the syringe plunger. The known syringe actuators are therefore not very versatile.

It would be advantageous to have syringe actuators that are more versatile with regard to the movement thereof.

To this end, the present invention discloses a syringe actuator which is characterised in that it has a holding clamp to hold the tube flange or the syringe plunger flange, by applying pressure simultaneously to both faces of the tube flange or of the syringe plunger flange.

The present invention discloses the holding of the syringe by means of pressure applied by a clamp simultaneously to both faces of a flange of the syringe, either only to both faces of the plunger flange, only to both faces of the syringe tube flange, or to both faces of both flanges.

One effect obtained by means of the present invention is the possibility of holding the entire syringe by means of the pressure applied to the flange. This allows additional non-fixed or slideable holding points to be provided on the tube. This makes the tasks of positioning and removing the syringe from the actuator far easier. It also allows the entire syringe to be moved in the actual axis of actuation of the plunger, without actuating the plunger. Further, it also makes it easier to use different means for holding the syringe tube.

Preferably, the actuator of the present invention will combine said clamp or clamps with a syringe tube holder. Preferably, the holder will have a housing to receive the syringe tube. More preferably, the going through housing will have two distal openings and a longitudinal opening connecting the two distal openings. In a similarly preferred manner, the holder will be made of elastomer, so that the holder can apply pressure to the syringe tube by resilient deformation of the walls of the housing. In preferred embodiments, the holder will have external projections to be handled by robotic arms or to be introduced in respective grooves of a holder support.

With regard to the clamp system, in a particularly preferred embodiment, said system comprises a U-shaped part which is situated between the most distal face of the flange of the syringe tube and the most distal face of the flange of the syringe plunger. The clamps may be completed by an actuator for applying pressure to the proximal face of the flange of the syringe plunger. It may also, preferably, be completed by a moveable actuator situated on the face of said U-shaped part in contact with the distal face of the syringe plunger.

In the present invention, the distal or most distal face is understood to be the faces that are furthest from the body of the syringe tube, and the proximal or most proximal face means the faces closest to the body of the syringe tube.

For a better understanding, the accompanying drawings show an embodiment of the object of the present invention as an explanatory but not a limiting example.

FIGS. 1 to 12 have been shown schematically to make it easier to understand the invention.

Figure 1:
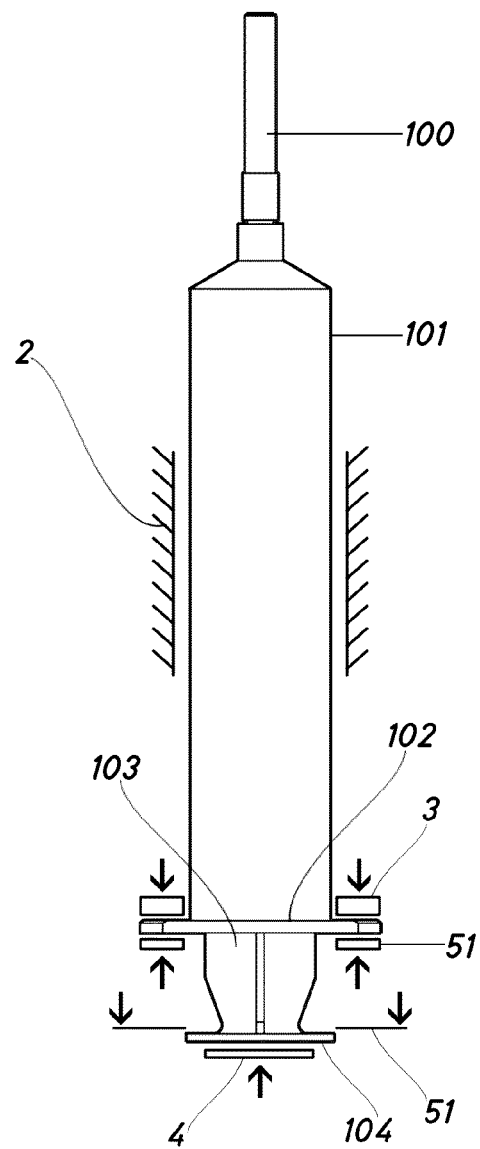
FIG. 1 is a diagrammatic view of a syringe which can be actuated by means of an automatic actuator according to the present invention.
Figure 2:
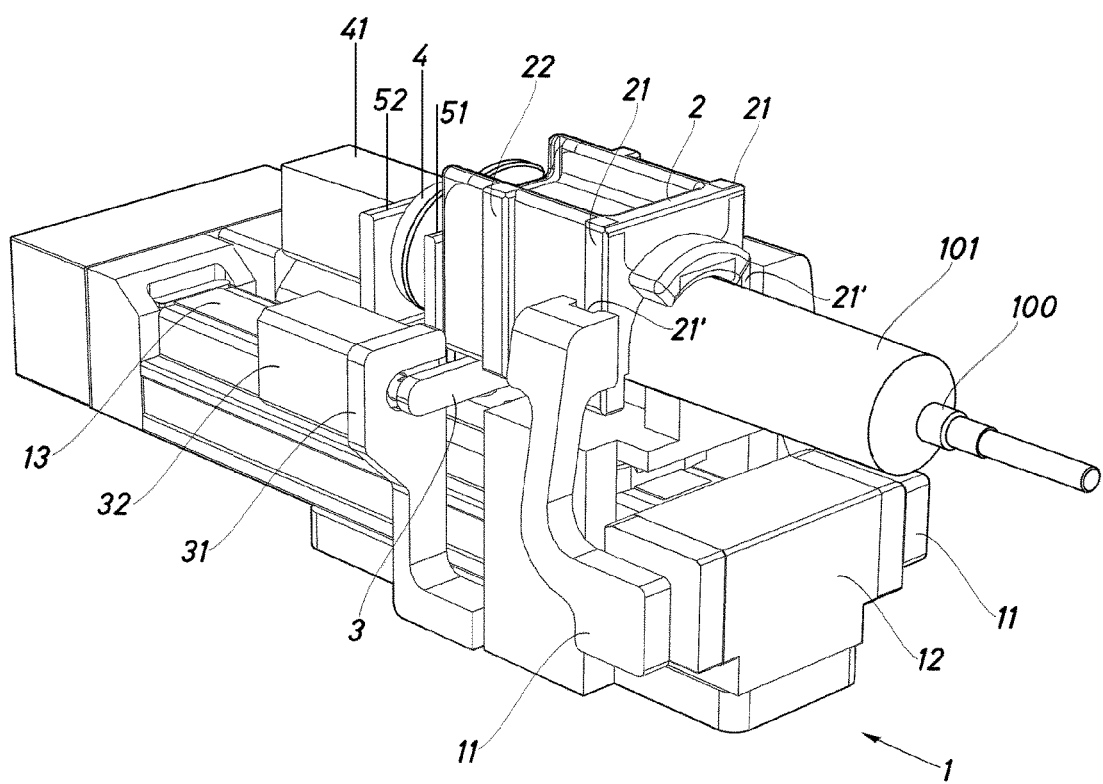
FIG. 2 is a perspective view of an embodiment of a robotic syringe actuator according to the present invention. The syringe has been shown in the horizontal position, although it will be understood that it can be placed in the vertical position or in any other spatial position.
Figure 3:
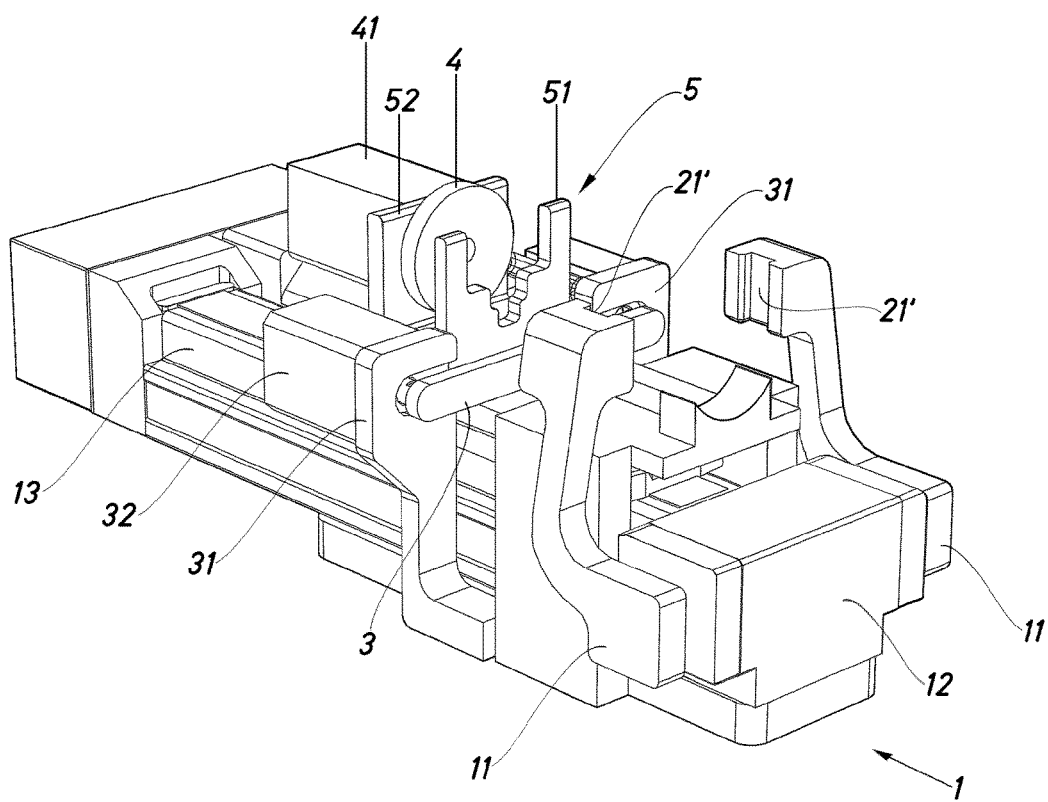
FIG. 3 is a perspective view of the actuator of FIG. 2 in which both the syringe and the part that forms the syringe tube holder have been omitted.
Figure 4:
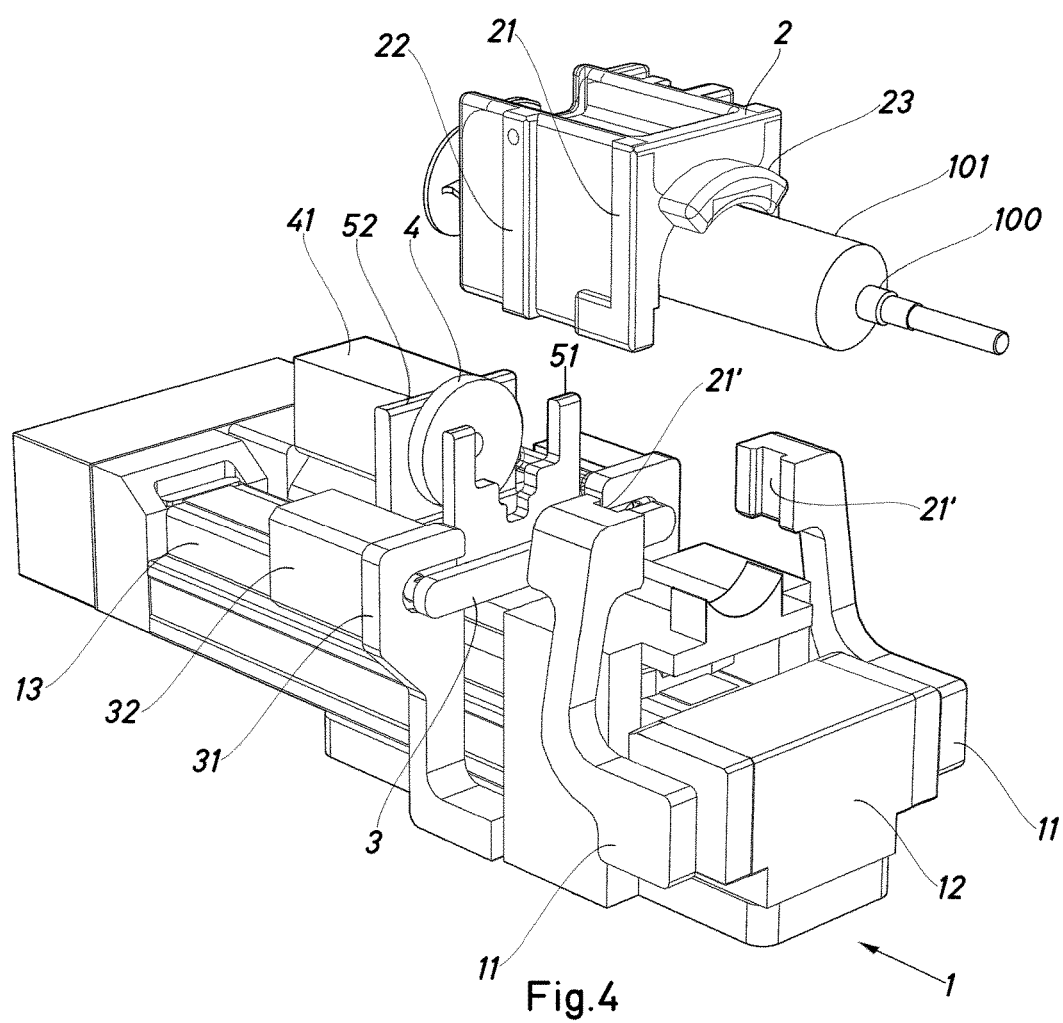
FIG. 4 is a perspective view of the actuator of FIG. 3 in which a syringe and said holder are shown separated from the actuator.
Figure 5:
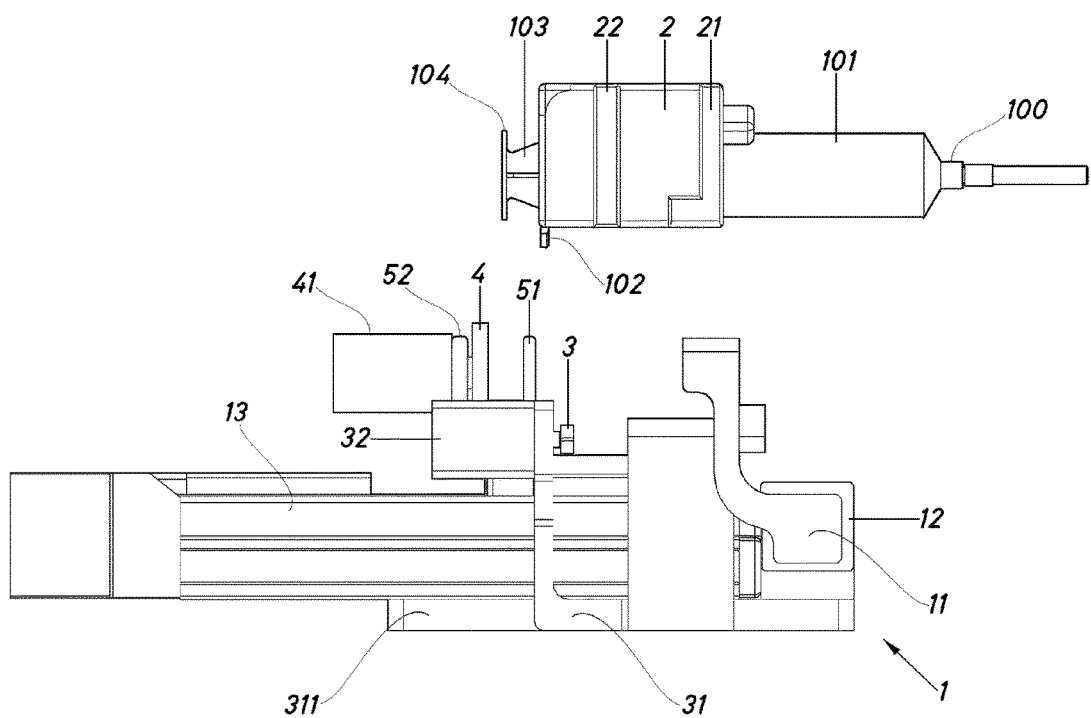
FIG. 5 is a view in side elevation of the view of FIG. 4.

In FIG. 1, actions on a syringe according to embodiments of the present invention are shown schematically.

The syringes, as shown in FIG. 1, comprise a needle zone (shown covered with a protective cap 100 in the figures), a syringe tube 101 through which a plunger 103 can slide, the syringe tube ending distally in a flange 102. The plunger 103 in turn has a flange 104 at the distal end thereof which facilitates actuation of said plunger.

According to the present invention, clamp elements 3, 51, 4 are provided, which have the ability to move and which are capable of applying pressure simultaneously to both faces of the flange 102 of the tube 101 or to both faces of the flange 104 of the plunger 103. In the example shown, all the clamp elements 3, 51, 4 are able to move in the axial direction of the syringe, however, it will be understood that the only requirement is that the elements act as a clamp on both sides of each of the flanges, and therefore one of each pair of elements forming a clamp could, if necessary, be fixed. In addition, although two clamps have been shown, one on each of the flanges 102, 104, it would be possible to use a single clamp. The actuator may also have a holding element 2 for the tube 101 which surrounds the walls thereof. The holding element 2 has been shown schematically in FIG. 1 in the form of a housing, and has two positions, one in which pressure is applied to the walls of the tube 101 of the syringe and the other in which said tube is released. Finally, it is possible that the movement of each of the clamp elements 3, 51, 4 is independent of the combined clamp elements, which can allow the plunger 103, for example, to be actuated independently of the tube 101 with economy of means.

FIGS. 2 to 12 show an embodiment of the syringe actuator device of the present invention from different points of view and in different actuation situations. In all the figures, elements that are similar or the same have been shown with identical numerals, and an exhaustive description of each of them, figure by figure, will therefore not be given.

A robotized actuator 1 for syringes, which has different driving elements (not shown) for actuating the different elements, arms and actuators with which it is provided is shown in the figures.

The device has two arms 11 which take and hold a part which acts as the holding element 2 of the syringe. Said arms 11 can be actuated by the actuator 12 which can, for example, open or close them.

The holder 2 is a part made of elastomer which has an inner housing suitable for receiving a syringe. As it is made of an elastomer material, the holder 2 can be designed so that when it applies pressure to the tube 101 the walls of the holder are deformed, in such a way that, owing to said deformation of its walls, the holder 2 holds the syringe by pressure. The elastomeric properties of the material of the holder 2 can also be used to allow the same holder 2 to be used for syringes with tubes of different diameters. The holder 2 has lateral emerging zones 21 which are used for holding said holder by the combined grooves 21' of the arms 11 of the actuator 1. Moreover, the holder 2 comprises other external projections 22 that serve to be introduced respectively within grooves 61 arranged in a support 62 for syringe holders 2, as it will be explained further on the description with reference to FIGS. 13 to 16.

The actuator 1 also has a second pair of arms 31, which in the case shown can slide along the runner 311 and which terminate at the free end thereof in a bar 3 actuated by a driving element 32 (for example, a pneumatic cylinder) which provide the bar with precision movement in the axial direction of the syringe. This bar 3 is one of the elements that form the clamp acting on the flange 102 of the tube 101 of the syringe. As it can be actuated, the clamp element can accept syringes with different thicknesses of flange 102.

The actuator 1 also has a part of U-shaped cross section 5 which has two vertical emerging walls 51 and 52 which form the legs of the U-shape. The emerging wall 51 has a cutout zone which allows the syringe plunger to be housed but which has smaller dimensions than the flanges of the tube 102 and of the plunger 104 of the syringe, and is arranged on the distal face of the flange 102 of the tube 101 of the syringe. Thus, the upper face of the emerging wall 51 and the bar 3 form the elements that clamp the flange 102 of the tube 101 of the syringe. The emerging wall 52 for its part has a disk 4 which can be actuated in the axial direction of the syringe by means of a driving element 41. The elements that form the clamp on the flange 104 of the plunger 103 are the emerging wall 51 and the disk 4 which is situated on the emerging wall 52. The forward actuation of the disk 4 by the driving element 41 allows the plunger 103 to be actuated so as to introduce said plunger into the tube 101 of the syringe. It also allows a clamping action to be applied to flanges of different thicknesses. The part 5 with the emerging walls 51, 52 thereof can slide on the runner 13 through the carriage 14. This movement is independent of the movements of the bar 3 and of the actuation of the disk 4. The independence from the movement of the bar 3 allows the plunger 103 to slide outside the tube 101 whilst the tube 101 is held by the holder 2, whereas the actuation of the disk 4 allows pressure to be maintained on the flange 104 of the plunger 103 at all times.

Figure 7:
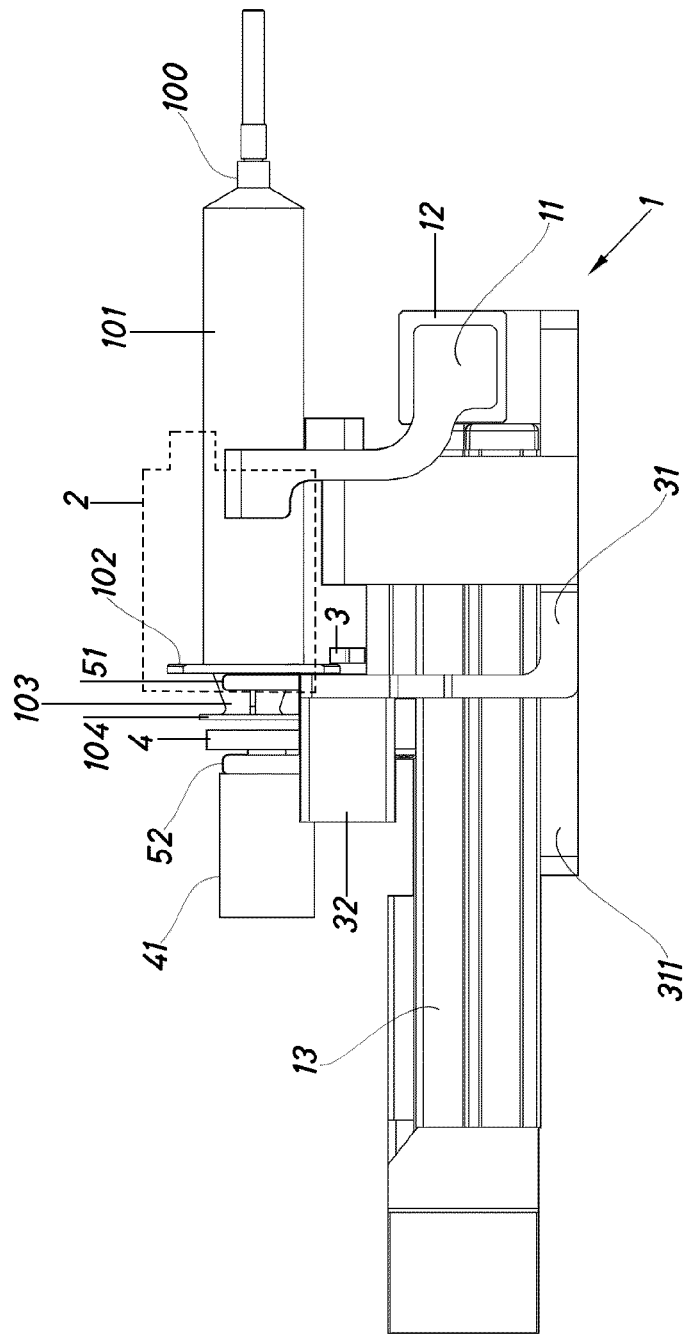
FIG. 7 is a side view of FIG. 6 in which the elements that form the clamp that holds the flange of the syringe tube have been actuated and the outer contour of the syringe tube holder has been shown as a dashed line.

FIG. 7 shows how the bar 3 and the upper face of the emerging wall 51 exert a clamping effect on the flange 102 of the tube 101 of the syringe. To do this, the driving element 32 of the bar and the driving element 41 are suitably actuated which causes the U-shaped part with the emerging walls 51, 52 thereof and the disk 4 to slide along the runner 13.

Figure 8:
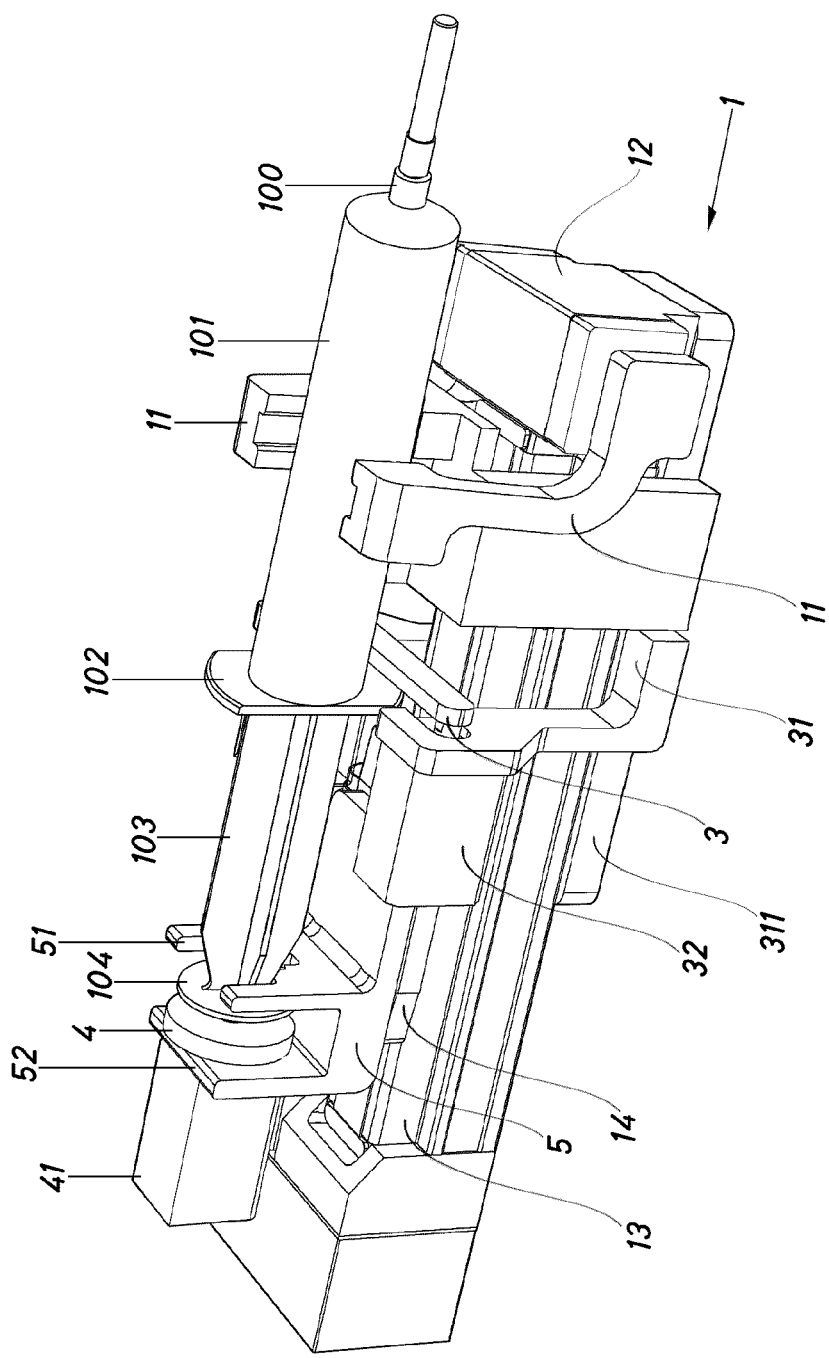
FIG. 8 is a perspective view equivalent to that of FIG. 6 in which the holder has not been shown and in which the elements of the actuator have been actuated to extend the syringe plunger.
Figure 9:
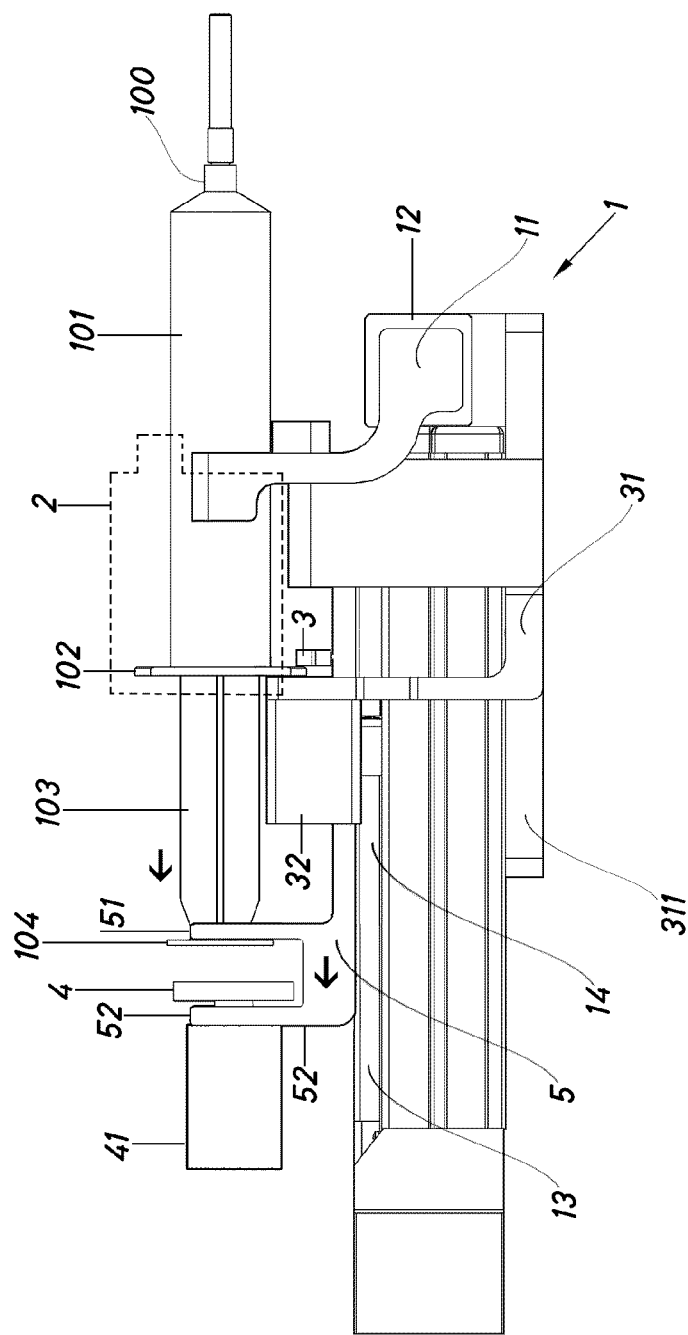
FIG. 9 is a view in side elevation of FIG. 8.
Figure 10:
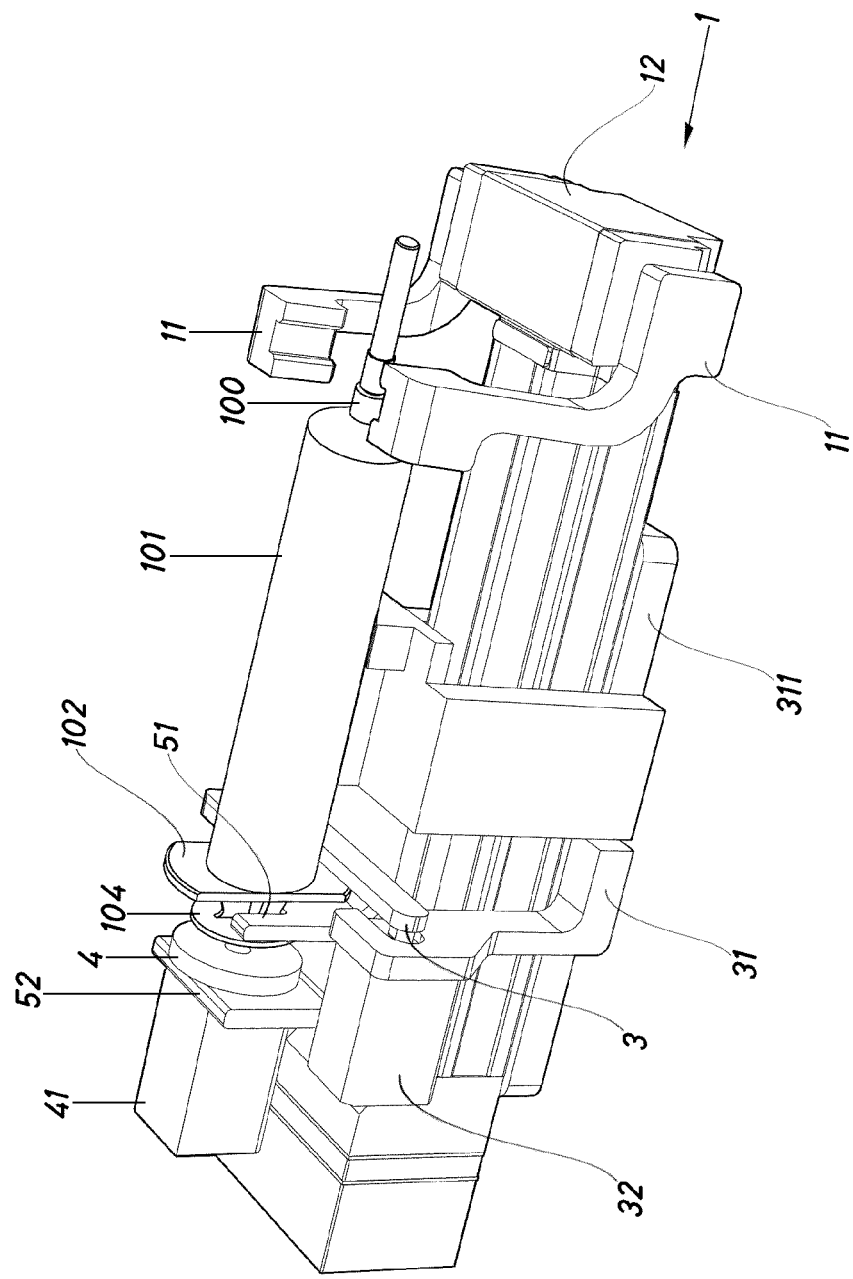
FIG. 10 is a perspective view of the view of the actuator of FIG. 8 in which the elements that form a clamp on the flange of the syringe body have been actuated and the entire syringe has been made to slide by the simultaneous movement of said elements.
Figure 11:
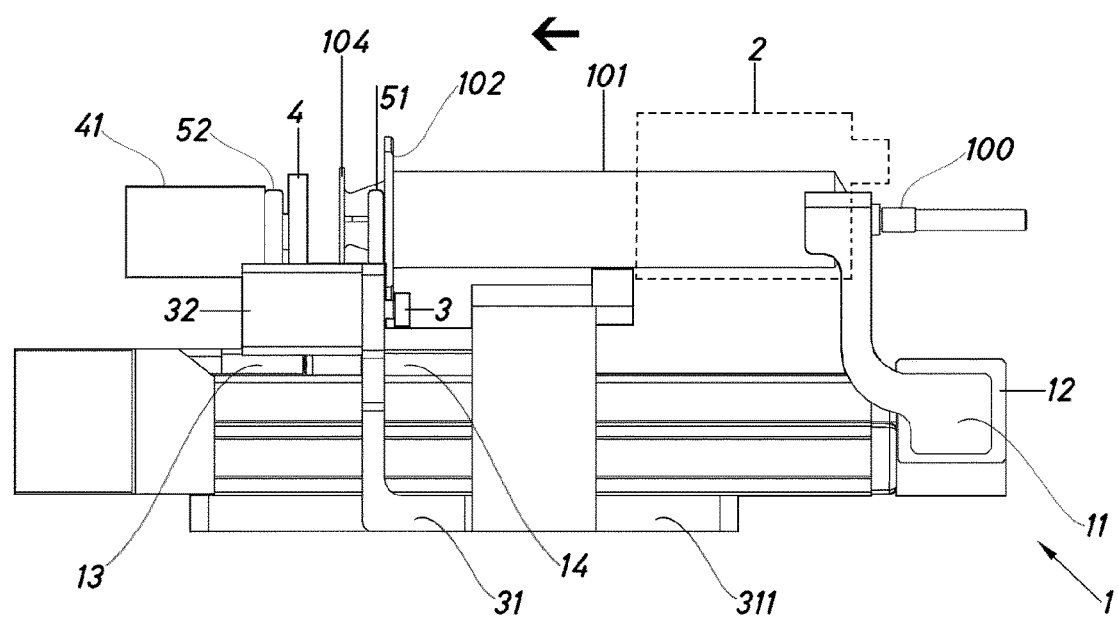
FIG. 11 is a view in side elevation of FIG. 10.

From said position, as shown in FIGS. 7 and 8, if the U-shaped part assembly 5 is made to slide along the runner 13, the plunger 103 is actuated toward the outside of the tube 102. As can be seen in the figures, the disk 4 has not been actuated, but it could be, until the disk 4 is in contact with the distal face of the flange 104 of the plunger 103 so that it applies additional holding power to the syringe. The plunger can be returned to the initial position thereof by the reverse travel of the part 5. The final portion of the travel of the flange 104 of the plunger 103 between the emerging walls 51, 52 is effected by the disk 4 being actuated by the driving element 41.

Figure 6:
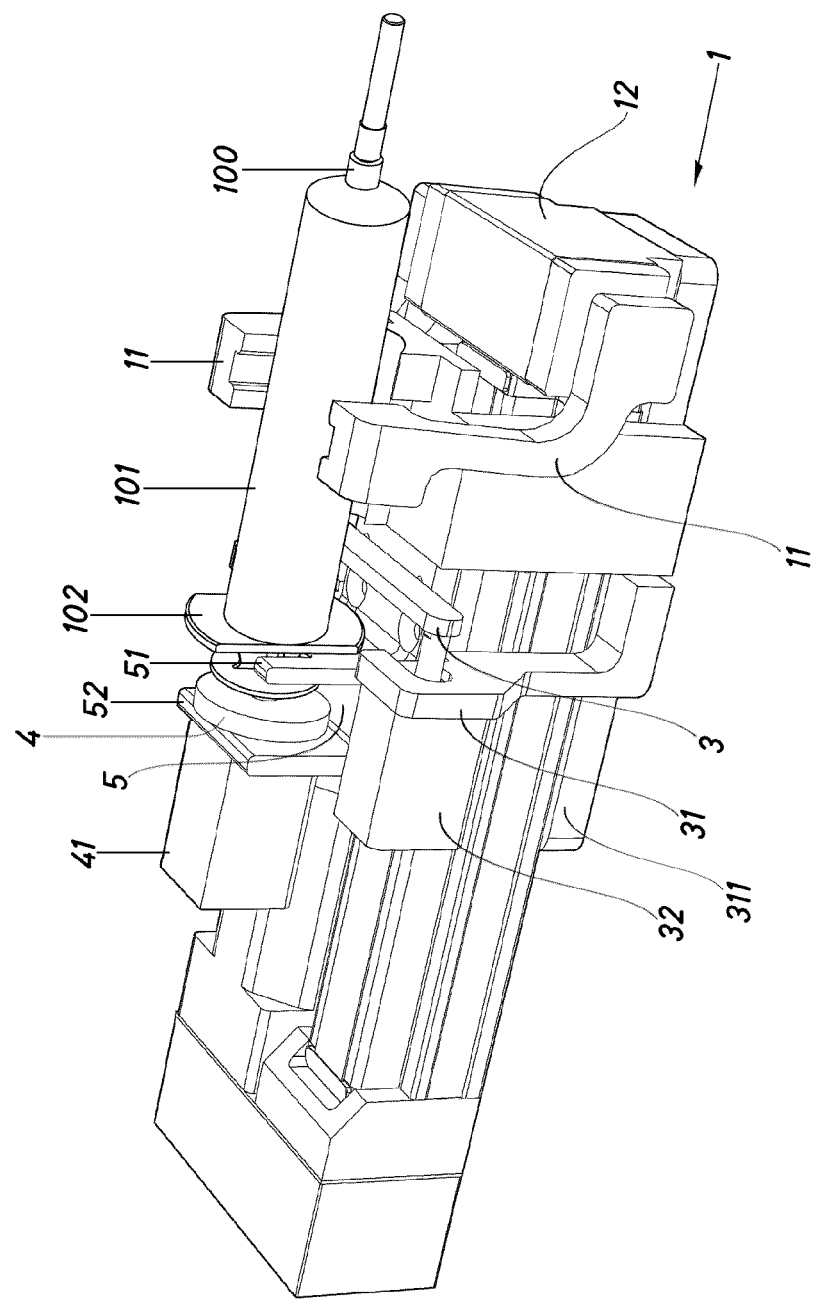
FIG. 6 is a perspective view of the robotic actuator of FIG. 2 showing the syringe, but not the syringe tube holder, and the elements that form the clamps that hold the flanges of the syringe have been shown in the open position, to make it easier to see the different elements and their spatial arrangement.

Starting from the position of FIG. 6, if the part 5 is actuated along the runner 13, but the second pair of arms 31 is actuated in a simultaneous and coordinated way along the runners 311, then what happens is that the entire syringe moves in an axial direction, sliding relative to the holder 2. This allows syringes to be removed from and positioned in the holder 2 without having to handle them by means of a holder 2.

The holding of one of the flanges also allows the arms 11 that support the holder 2 to be opened without having to be held previously by an external element.

Figure 12:
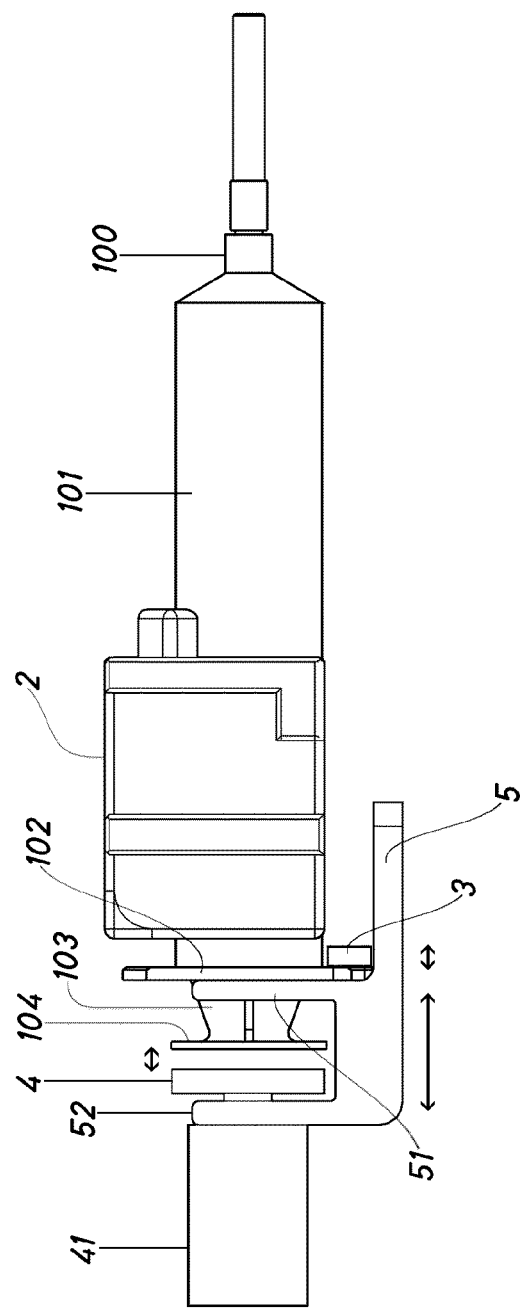
FIG. 12 is a view in side elevation that shows only a syringe, a syringe holder and the elements that act as a clamp and/or actuators on the different faces of the flanges of the syringe tube and of the syringe plunger.

FIG. 12 shows in isolation the elements that participate in holding the syringe and which have been shown in FIGS. 2 to 12. The elements that clamp the flange 102 are the bar and the proximal face of the emerging wall 51. The elements that clamp the flange 104 are the distal face of the emerging wall 51 and the disk 4. In addition, both the emerging wall 51 and the disk 4 can actuate the flange 104 in order to move the plunger 103 along the tube 101 of the syringe.

In FIGS. 13 to 16 an exemplary embodiment of a procedure that is carried out by the syringe actuator device 1, object of the present invention, is shown. In all the figures, elements that are similar or the same have been shown with identical numerals, and an exhaustive description of each of them, figure by figure, will therefore not be given.

Figure 13:
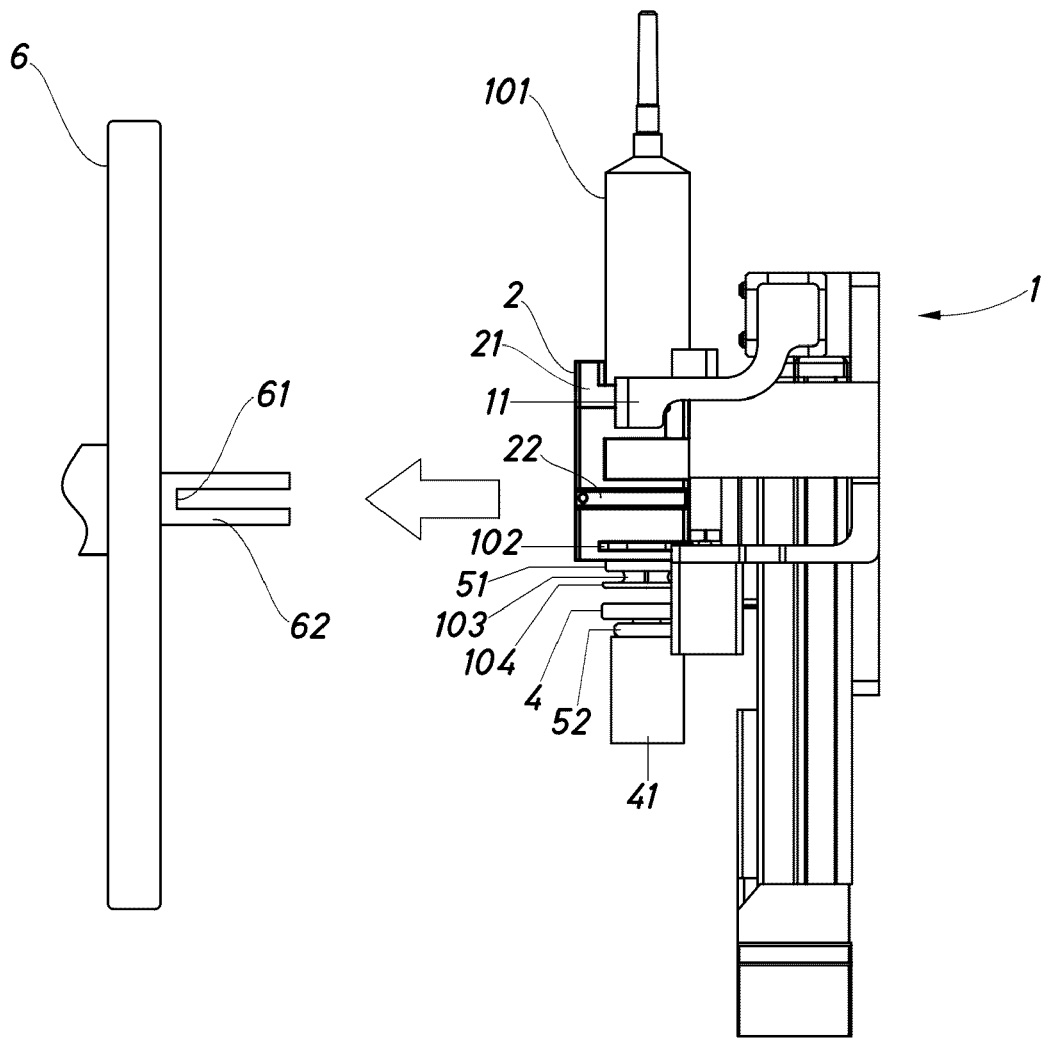
FIG. 13 is a view in side elevation of the actuator prepared to arrange and to fix the holder-syringe assembly in a support adapted for holders.

FIG. 13 shows the actuator 1 supporting by their respective arms 11 the syringe holder 2 by their respective lateral emerging zones 21. Additionally, the holder 2 is holding the body 101 of the syringe only by the walls of the inner housing of said holder. That is, in this case, none of the above-mentioned clamp elements are supporting any peripheral flange of the syringe. According to FIG. 13, the actuator 1 is approaching to an area where there is a plate 6 having at least a support 62 for syringe holders 2 with the intention to place and fix the holder 2 within the groove 61 of said support 62 of said plate 6.

Figure 14:
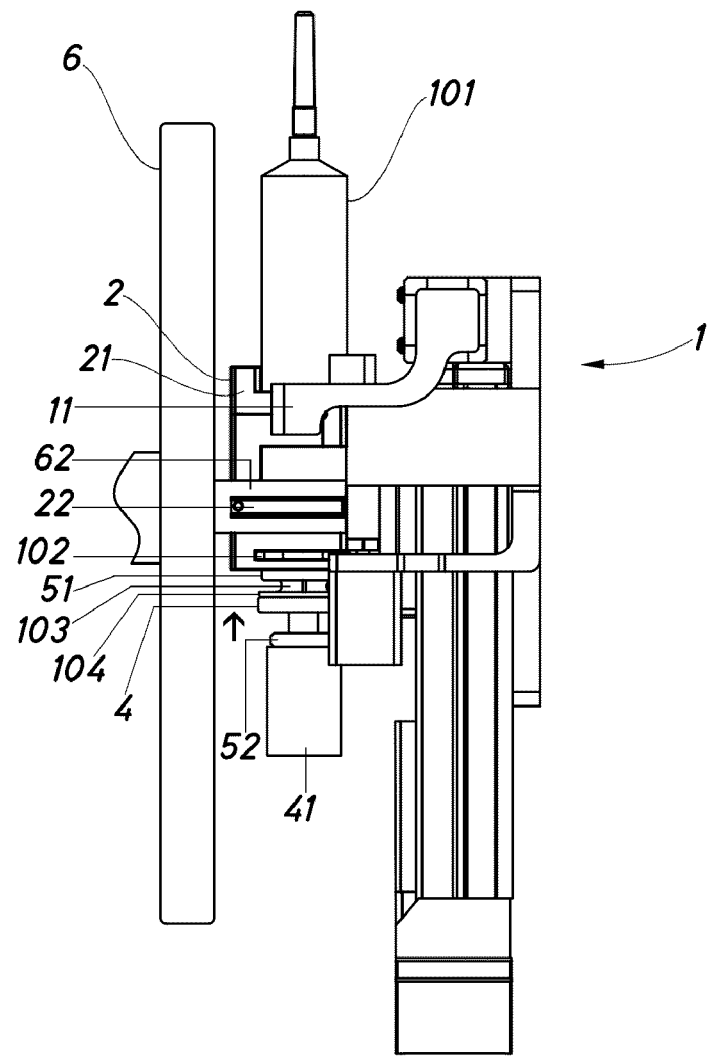
FIG. 14 is a view in side elevation of the actuator prepared to hold the plunger flange by pressing the distal face of said plunger flange against one of the two walls of the U-shaped part.

Subsequently, FIG. 14 shows how the actuator 1 has fitted lateral emerging zones 22 respectively within the groove 61 of the support 62. Additionally, disk 4 is ready to be driven for pressing the distal face of the flange 104 of the plunger 103 toward the distal face of emerging wall 51, so as to exert a clamping of the syringe.

Figure 15:
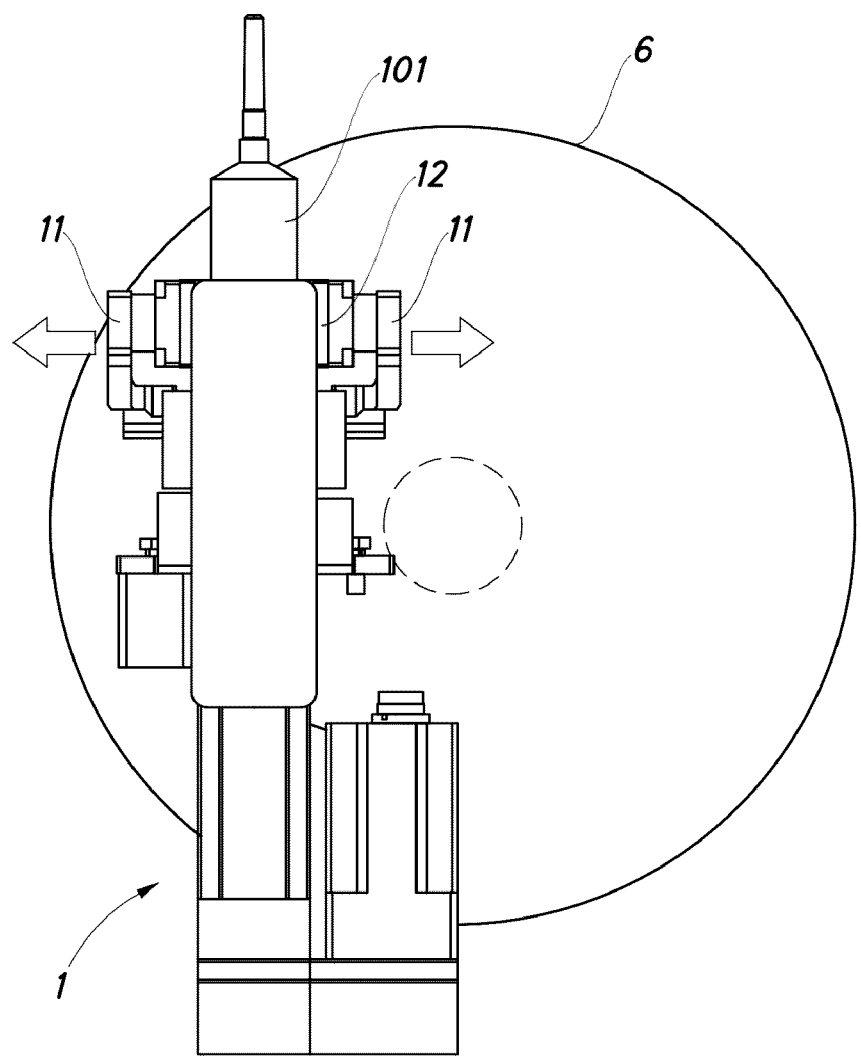
FIG. 15 is a view in back elevation of the actuator releasing the projections of the holder by means of their arms respectively.

Subsequently, FIG. 15 shows how arms 11 are opened driven by actuator 12, releasing lateral emerging zones 21 respectively of holder 2.

Figure 16:
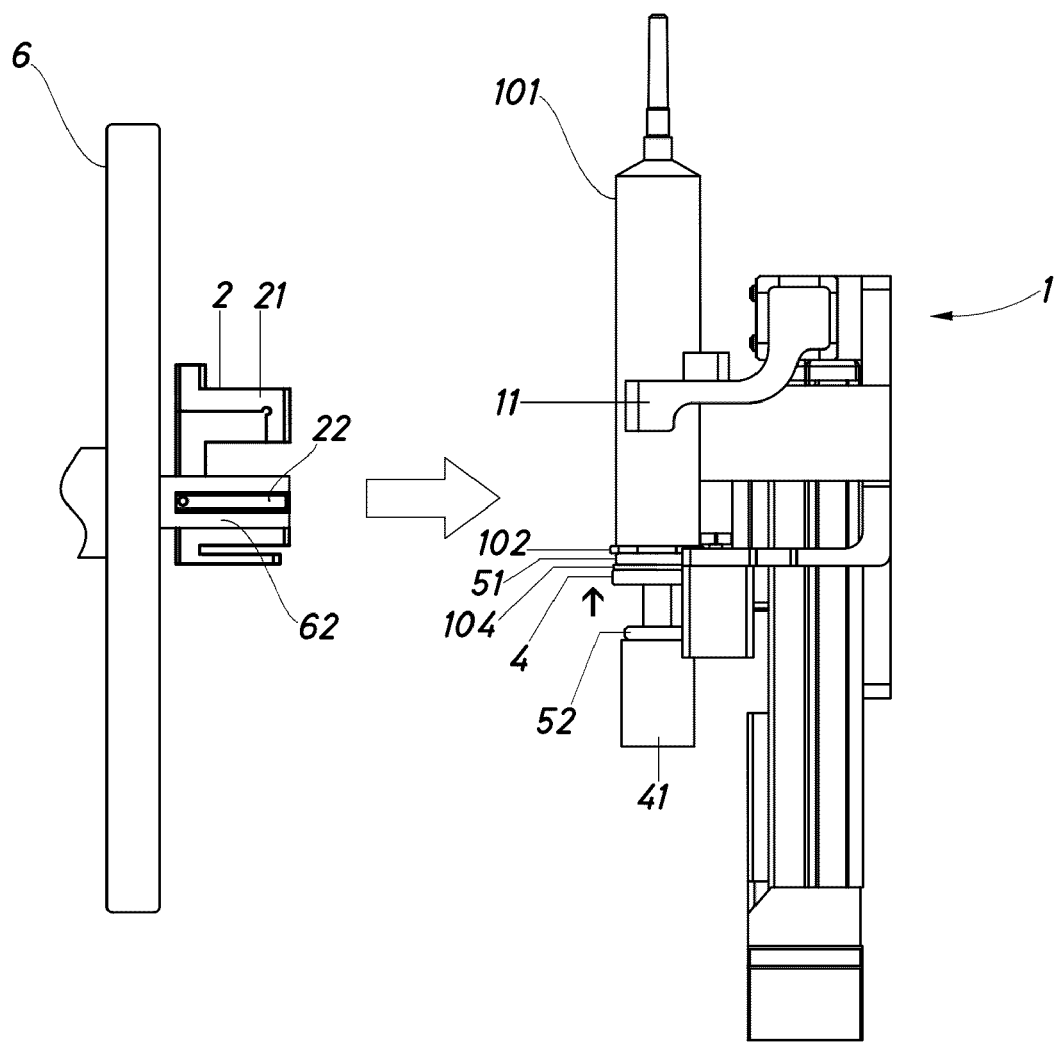
FIG. 16 is a view in side elevation of the actuator showing how the actuator moves back leaving the holder within the support for holders and at the same time only carrying the syringe.

Then, and as illustrated in FIG. 16, actuator 1 moves back, leaving holder 2 fixed in the support 62, but carrying with it the syringe due to the pressure exerted by disk 4 on the distal face of the flange 104 of the plunger 103 toward the distal face of emerging wall 51, allowing the clamping of the syringe.

Due to this procedure, actuator, after a given operation using the assembly (holder 2, syringe) can then carry only the syringe. In this way, the actuator can, for example, be positioned below a waste for syringes and drop the syringe within said waste by means of an action of disk 4 axially opposite to flange 104 of plunger 103.

Numerous variations are possible with respect to what has been shown in the examples given. For example, the motor elements may be pneumatic cylinders, but they may also be motors. Also, the part 5 with a U-shaped cross section may be a single part in the form of a single emerging wall with the ability to move which can be moved in order to collaborate in performing the clamping action on one of the flanges of the syringe.

Although the invention has been described with respect to examples of preferred embodiments, these should not be considered as limiting the invention, which will be defined by the widest interpretation of the following claims.

What is claimed is:

1. A robotized syringe actuator apparatus, comprising:
   a first holding clamp configured to hold a tube flange of a syringe by applying pressure simultaneously to both faces of the tube flange;
   a second holding clamp configured to hold a plunger flange of the syringe by applying pressure simultaneously to both faces of the plunger flange, and
   a holder configured to hold a syringe tube which has a housing for receiving the syringe tube;
   wherein:
   the first holding clamp comprises a bar and a first vertical emerging wall, and
   the second holding clamp comprises the first vertical emerging wall and a disk movably coupled to a second vertical wall.

2. The robotized syringe actuator apparatus according to claim 1 wherein the first holding clamp and the second holding clamp are configured to apply pressure simultaneously to both faces of each flange of the syringe, either only to the plunger flange, only to tube flange, or to both the plunger flange and the tube flange.

3. The robotized syringe actuator apparatus according to claim 1, wherein the holder is made of an elastomer material.

4. The robotized syringe actuator apparatus according to claim 1, wherein the holder has external projections to be handled by robotic arms.

5. The robotized syringe actuator apparatus according to claim 1, wherein:
   the first vertical emerging wall and the second vertical emerging wall form legs of a U-shaped part, and
   the first vertical emerging wall is configured to be situated between the tube flange of the syringe and the plunger flange of the syringe, and to move therebetween when the syringe is set to the robotized syringe actuator apparatus.

6. The robotized syringe actuator apparatus according to claim 5, further comprising an actuator for applying pressure to a face of the plunger flange facing toward the syringe tube.

7. The robotized syringe actuator apparatus according to claim 5, further comprising a moveable actuator situated on a face of said U-shaped part in contact with the plunger flange through the disk.

8. A method for actuating a syringe with the robotized syringe actuator apparatus according to claim 1, comprising the steps of:
   providing the syringe;
   holding the tube flange with the first holding clamp or the syringe flange with the second holding clamp; and
   receiving the syringe tube in the housing of the holder, thereby holding the syringe tube with the holder;
   wherein the pressure is applied simultaneously to both faces of each flanges either only to the tube flange or to the plunger flange.

9. The method according to claim 8 wherein the pressure is applied simultaneously to both faces of each flanges either only to the tube flange or to the plunger flange, or to both the tube flange and the plunger flange.

10. The method according to claim 8, wherein the holder is made of an elastomer material.

11. The method according to claim 8, wherein the robotized syringe actuator apparatus comprises robotic arms and the holder has external projections, further comprising handling the external projections by the robotic arms.

12. The method according to claim 8, further comprising moving the first vertical emerging wall between the tube flange of the syringe and the plunger flange of the syringe.

13. The method according to claim 12, wherein pressure is applied to a face of the plunger flange facing toward the syringe tube.

14. The method according to claim 12, further comprising moving an actuator situated on a face of said U-shaped part in contact with the plunger flange through the disk.

\* \* \* \* \*

UNITED STATES PATENT AND TRADEMARK OFFICE
CERTIFICATE OF CORRECTION

PATENT NO. : 9,795,535 B2
APPLICATION NO. : 14/718870
DATED : October 24, 2017
INVENTOR(S) : Jean-Philippe Aguerre Page 1 of 1

It is certified that error appears in the above-identified patent and that said Letters Patent is hereby corrected as shown below:

On the Title Page

Please add "Foreign Application Priority Data" as follows:
May 21, 2014 (ES) – P 201430746

Signed and Sealed this
Tenth Day of July, 2018

Andrei Iancu
*Director of the United States Patent and Trademark Office*